(12) United States Patent
Hasenzahl

(10) Patent No.: US 8,127,420 B2
(45) Date of Patent: Mar. 6, 2012

(54) DENTAL MACHINING DEVICE AND METHOD FOR MONITORING SEALING ELEMENTS IN DENTAL MACHINING DEVICES

(75) Inventor: Thomas Hasenzahl, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 1034 days.

(21) Appl. No.: 12/010,792

(22) Filed: Jan. 30, 2008

(65) Prior Publication Data

US 2008/0233536 A1    Sep. 25, 2008

Related U.S. Application Data

(60) Provisional application No. 60/906,180, filed on Mar. 12, 2007.

(30) Foreign Application Priority Data

Mar. 12, 2007   (DE) .......................... 10 2007 012 232

(51) Int. Cl.
*B23Q 17/00* (2006.01)
*A61C 1/00* (2006.01)
(52) U.S. Cl. ...................................... 29/407.05; 433/89
(58) Field of Classification Search ............... 29/407.05, 29/407.08, 896.1, 709; 433/76, 49, 89, 51
See application file for complete search history.

(56) References Cited

U.S. PATENT DOCUMENTS 7,234,938 B2 *  6/2007  Bodenmiller ................... 433/51

FOREIGN PATENT DOCUMENTS

| AT | 401142 | 6/1996 |
|---|---|---|
| DE | 3438755 | 4/1986 |
| DE | 272899 | 10/1989 |
| DE | 4030175 | 3/1992 |
| DE | 4419660 | 12/1995 |

OTHER PUBLICATIONS

English Abstract of DE4030175.
English Abstract of DE4419660.
English Abstract of AT401142.
English Abstract of DE3438755.

* cited by examiner

*Primary Examiner* — John C Hong
(74) *Attorney, Agent, or Firm* — Dykema Gossett PLLC

(57) ABSTRACT

A dental machining device (1) having at least one shaft (2) which projects into a machining chamber (4) and is displaceable in both axial and radial directions includes a sealing element (7) having at least two axially spaced sealing lips (8, 9) bearing against the shaft (2) in its peripheral direction and enclosing an annular chamber (10) with the shaft (2). At least one fluid conduit (11) opens into the annular chamber (10) to supply a fluid (16) thereto. A pressure sensor (14) is provided for detecting a state variable of the fluid, which is detected and held ready for transmission to a control unit (14").

12 Claims, 2 Drawing Sheets

DENTAL MACHINING DEVICE AND METHOD FOR MONITORING SEALING ELEMENTS IN DENTAL MACHINING DEVICES

CROSS-REFERENCE TO RELATED APPLICATION

This application derives from U.S. Provisional Application Ser. No. 60/906,180, filed Mar. 12, 2007, the priority of which is claimed. The priority of German Application 102007012232.4, filed Mar. 12, 2007, is also claimed.

BACKGROUND OF THE INVENTION

The invention relates to a dental machining device that includes at least one axially and radially displaceable shaft projecting into a machining chamber and having a sealing element for sealing the shaft. The invention further relates to a method for monitoring such sealing elements.

DESCRIPTION OF THE PRIOR ART

Shaft sealing elements that are designed for movements in a single dimension, for translatory or rotary movements of a shaft, are known in the prior art. Known sealing elements for translatory movements include, but are not limited to, gland seals, piston rings, and bellows. Sealing elements for rotary movements include, but are not limited to, radial shaft seals, axial shaft seals, axial face seals, and rotary turrets.

A disadvantage of the sealing elements known in the prior art is that they wear quickly with alternating or superimposed translatory and rotary movements and lose or never even attain the required degree of tightness.

Worn sealing elements pose a significant problem for a dental machining device, especially when involving machining of ceramic materials by grinding or milling. The resultant grinding dust can penetrate through defective seals into the bearing area of a shaft of the machining device and lead to irreparable damage of the bearings in a very short time.

It is therefore an object of the invention to provide a dental machining device and a method for monitoring the sealing elements in a dental machining device that permit optimal, low-wear sealing in the case of radial as well as axial motion, in order to prevent damage from grinding dust penetrating into the shaft bearings.

SUMMARY OF THE INVENTION

In the dental machining device of the invention which includes at least one axially and radially displaceable shaft projecting into a machining chamber and having a sealing element for sealing said shaft, the sealing element has at least two axially spaced sealing lips bearing peripherally against the shaft and forming an annular space therewith. At least one fluid conduit opening into said annular space is provided for supplying a fluid. Furthermore, means for determining a state variable of the fluid are provided.

The efficacy of the seal during operation can be verified by said means.

Advantageously pressurizing device for delivering the fluid, say, a pump, a compressor, or a pressure reservoir, is connected to the fluid conduit.

The fluid in the annular space can advantageously be under excess pressure, preferably ranging from 1 and 500 mbar, and the front sealing lip can advantageously be biased to such an extent that said sealing lip also bears against the shaft under excess pressure.

The means for determining a state variable of the fluid can advantageously comprise a pressure sensor or a flowmeter.

The means for determining a state variable of the fluid can advantageously have an computer interface, by means of which information on state variables of the fluid can be transmitted.

The sealing element comprising the at least two sealing lips can advantageously be designed as a single unit.

The state variable can advantageously be selected from the pressure and/or the rate of volumetric flow of the fluid.

The fluid used is advantageously a liquid, preferably water, or a gas, preferably air.

Another object of the invention is to provide a method for monitoring sealing elements for axially and radially displaceable shafts in a dental machining unit, in which the sealing element comprises at least two axially spaced sealing lips bearing peripherally against the shaft and forming an annular space therewith. The method comprises the following steps: charging the annular space with a fluid via a fluid conduit, determining a state variable of the fluid, and holding a value corresponding to one of the state variables of the fluid or to a change in a state variable of the fluid in readiness for transmission to a control unit.

A conclusion regarding the condition of the sealing element can thus be made on the basis of the state of the fluid.

The annular space is advantageously charged with the fluid by means of a pressurizing device.

The fluid can be advantageously conducted into the annular space under excess pressure, preference being given to an excess pressure ranging from 1 to 500 mbar, and the front sealing lip can advantageously be biased to such an extent that said sealing lip also bears against the shaft under excess pressure.

It is especially advantageous for a warning signal to be emitted when a pressure drop occurs which exceeds a first threshold value but is lower than a second threshold value, and when a further pressure drop occurs which exceeds the second threshold value, grinding of a workpiece currently being machined is completed followed by a shutdown of the machining device.

BRIEF DESCRIPTION OF THE DRAWINGS

The method of the invention is now explained with reference to the drawings.

DESCRIPTION OF A PREFERRED EMBODIMENT

Figure 1:
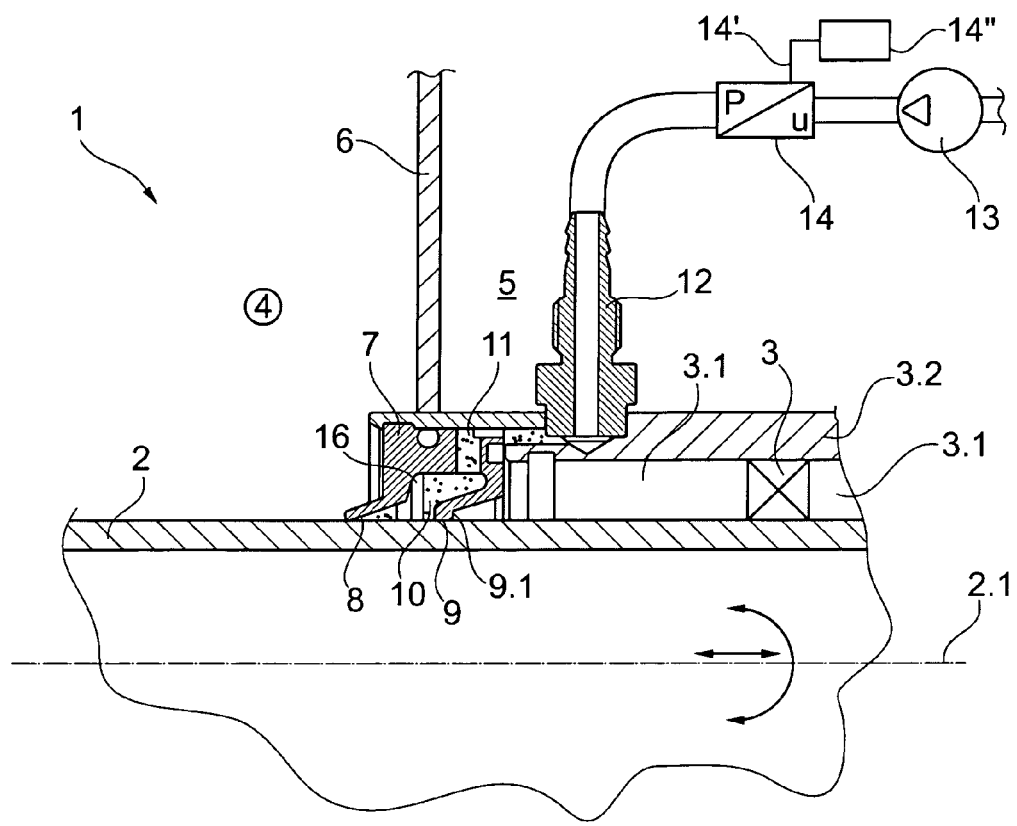
FIG. 1 shows a portion of a machining device incorporating a sealing unit of the invention.

FIG. 1 shows a portion of a dental machining device 1. The machining device 1 has a hollow shaft 2 which projects into a grinding chamber 4 from an inner bearing chamber 3.1 exhibiting bearings 3, which inner bearing chamber is delimited by the shaft 2 and a bearing mount 3.2. The grinding chamber 4 and an internal chamber 5 of the grinding machine are separated from each other by a partition 6 of the housing, see also FIG. 3.

The shaft 2 can serve as a holder for a workpiece to be machined (not shown) or as a guide for a machining tool (not shown), and it is axially displaceable and rotatable about a central axis 2.1.

A sealing unit comprising a sealing element 7 with two sealing lips 8, 9 is provided for sealing the bearings 3 of the shaft 2 against the grinding chamber 4. Together with the shaft 2, the two sealing lips 8, 9 form an annular space 10 radially surrounding said shaft 2.

The sealing element 7 is a single piece and is manufactured by machining and in-mold embossing. It is preferably made of a shape-memorizing polymer. A sealing element manufactured in this way will suffer less wear than a standard spring-loaded seal.

A fluid channel 11 extending to the outer circumference of the sealing element for charging the same with the supplied fluid 16 opens into the annular space 10. The fluid 16 used is basically a liquid or a gas. Air 16 is used in the pre-sent embodiment.

The air 16 is conducted to the fluid channel 11 through a connection 12 in the bearing mounting 3.2. The air 16 is supplied at a pressure of 300 mbar by a pressurizing device, which in this case is a compressor 13. The bias on the sealing lip 8 is set so that said front sealing lip 8 does not lift from the shaft 2 in spite of the excess pressure in the annular space 10, but instead sealingly bears against said shaft 2.

As another component of the sealing unit, a pressure sensor 14 is provided in the conduit system downstream of the compressor 1, which sensor emits a voltage signal as a function of the prevailing pressure 3. Said voltage signal is transmitted by an interface 14' to a control unit 14" for regulating the machining device 1, and the state can be shown on a display or analyzed.

The pressure sensor can be disposed in the annular space 10, the fluid channel 11, the connection 12, or the conduit leading to the compressor 13.

The sealing lips 8, 9 are shaped so that they point toward the grinding chamber 4 and form a cone-shaped boundary thereto, and the sealing lips have a certain degree of flexibility. The sealing lip 9 has an angled end area 9.1 in order to affix, say, a lock washer for the application of a spring bias. The sealing lips 8, 9 are shaped so that the excess pressure produced by the compressor 13 causes the sealing lip 9 to press against the shaft 2 while the sealing lip 8 is freed from pressure without, however, lifting from said shaft 2.

In the event of damage occurring to the front sealing lip 8 or, less frequently, to the rear sealing lip 9, a pressure drop exceeding the normal loss of pressure that always occurs during operation is caused by air 16 escaping from the annular space 10. This additional pressure drop is registered by the pressure sensor 14 and transmitted to the control unit 14". If need be, the control unit 14" can stop the grinding machine 1, depending on the pressure values, and thus protect the bearings from intrusive grinding dust. The defective sealing element 7 can be replaced by a technician. Furthermore, in the case of a damaged front sealing lip 8 the blocking air 16 under excess pressure has the function of blowing intrusive particles back out into the machining chamber 4 by means of an air stream flowing away from the annular space 10. The penetration of particles into the inner bearing chamber 3.1 is thus effectively avoided.

Figure 2:
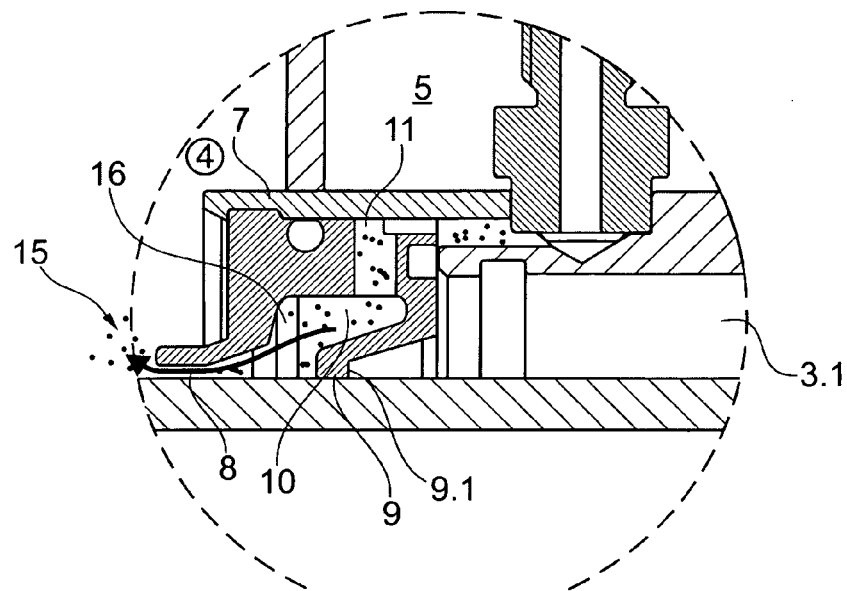
FIG. 2 shows a portion of the sealing unit illustrated in FIG. 1 in a worn condition.

FIG. 2 shows a magnified view of a detail of FIG. 1, in which the front sealing lip 8 of the sealing element 7 is worn, i.e., said sealing lip 8 no longer abuts against the shaft 2 because of the wear. In this case, there is the hazard of intrusion of grinding dust particles 15 into the annular space 10 unless countermeasures are taken. The excess pressure of the air 16 in said annular space 10, however, creates an air flow that blows at least some of the grinding dust particles 15 away from the defective site on said front sealing lip 8. Furthermore, the second sealing lip 9 prevents intrusion of the fluid as well as of any particles into the inner bearing chamber 3.1 and the interior space 5.

The pressure conditions in the annular space 10 are changed when the sealing lip 8 lifts from the shaft. The outflowing air stream leads to a drop in pressure, which is detected by the pressure sensor 14 (not shown in FIG. 2) in the annular space 10.

Depending on the pressure drop determined, various procedures can be carried out. A warning signal with the request to prepare for a seal replacement can be emitted with a pressure drop exceeding a first threshold value but lower than a second threshold value. In spite of the slightly increased loss of pressure in the seal, normal operation of the machine can continue until the seal is replaced.

With an increased loss of pressure in which the second threshold value is exceeded, a block that is in the process of being machined can be finished followed by a shutdown of the machining device, in order not to jeopardize production as well as to protect the machining device from greater damage.

Figure 3:
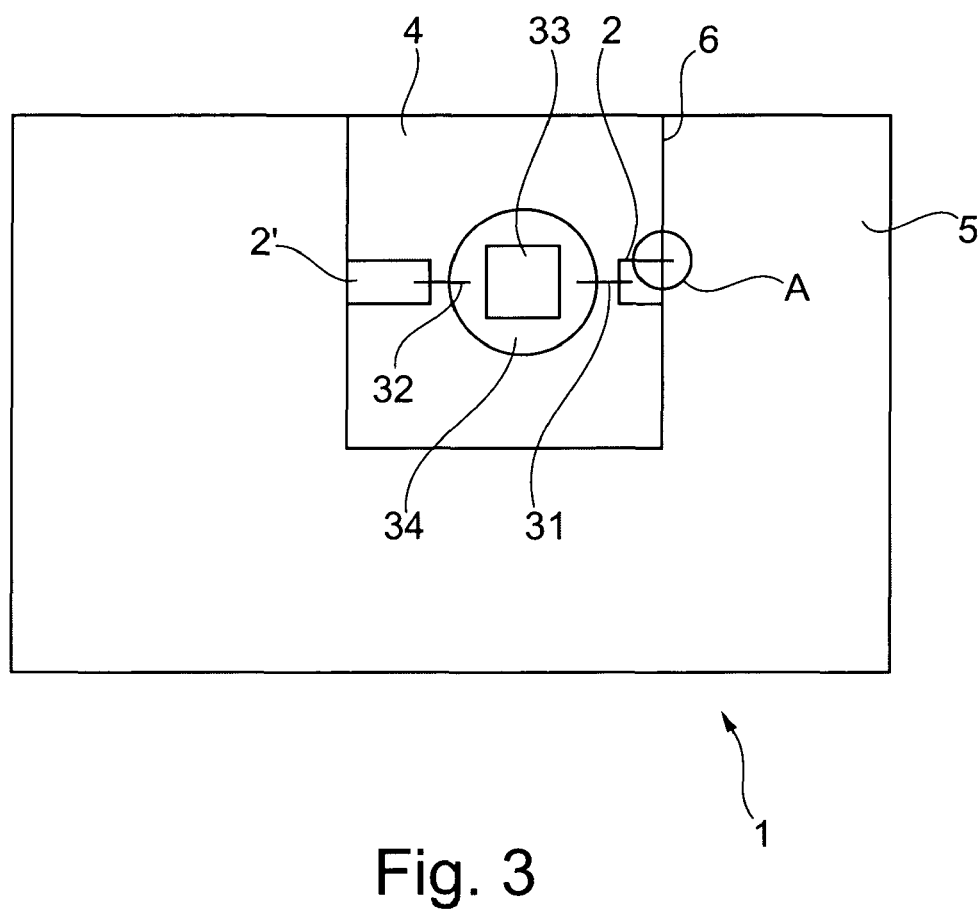
FIG. 3 shows a machining device incorporating a sealing unit of the invention.

The machining device 1 shown in FIG. 3 has machining tools 31, 32 arranged in a machining chamber 4 for machining a workpiece 33, which is held in a chuck 34. Said machining chamber 4 and the interior space 5 of the grinding machine are separated from each other by a partition 6 of the housing. The sealing element of the shafts 2, 2', which project into the machining chamber 4 as supports for the machining tools 31, 32, is shown as Detail A in the preceding figures.

The invention claimed is:

1. A dental machining device comprising at least one shaft which projects into a machining chamber and is displaceable in both axial and radial directions, and a sealing element for sealing said shaft, wherein said sealing element comprises:
at least two axially consecutively spaced sealing lips bearing against said shaft in a peripheral direction and enclosing an annular chamber with said shaft,
at least one fluid conduit opening into said annular chamber to supply a fluid thereto, and
means for detecting a state variable of said fluid.

2. The machining device according to claim 1, including a pressurizing device connected to said fluid conduit for supplying the fluid.

3. The machining device according to claim 2, wherein the fluid in the annular chamber is under a pressure between 1 and 500 mbar, and a front sealing lip exhibits a bias which is dimensioned such that the sealing lip also bears against the shaft under excess pressure.

4. The machining device according to claim 1, wherein said means for detecting a state variable of the fluid sensor comprise a pressure sensor or a flowmeter.

5. The machining device according to claim 1, wherein said means for detecting a state variable of the fluid comprise a computer interface concerning, via which information concerning state variables of the fluid can be transmitted.

6. The machining device according to claim 1, wherein said sealing element including the at least two sealing lips is in the form of a single unit.

7. The machining device according to claim 1, wherein the state variable is selected from the pressure and/or the volumetric flow rate of said fluid.

8. The machining device according to claim 1, wherein said fluid is a liquid or a gas.

9. A method for monitoring a sealing element for axially and radially displaceable shafts in a dental machining device according to claim 1, comprising the following steps:
(a) charging the annular chamber with a fluid via a fluid conduit,
(b) detecting a state variable of the fluid, and
(c) holding a value corresponding to a state variable of the fluid or changes in a state variable of the fluid ready for transmission to a control unit.

10. The method according to claim 9, wherein in step (a) the annular chamber said fluid is pressurized.

11. The method according to claim 9, wherein in step (a) said fluid is fed to said annular chamber under a pressure ranging from 1 and 500 mbar, and wherein one of said at least two sealing lips is a front sealing lip which is under a bias so as to bear against the shaft under excess pressure.

12. The method according to claim 9, wherein when a pressure drop exceeds a first threshold value but is below a second threshold value, a warning signal is delivered, and when an increased pressure drop exceeds said second threshold value, grinding of a workpiece currently being machined is completed, followed by a shutdown of the machining device.

* * * * *